United States Patent
Sugiyama et al.

(10) Patent No.: US 10,357,216 B2
(45) Date of Patent: Jul. 23, 2019

(54) MAMMOGRAPHY APPARATUS

(71) Applicant: Toshiba Medical Systems Corporation, Otawara-shi (JP)

(72) Inventors: Atsuko Sugiyama, Nasushiobara (JP); Yoshimasa Kobayashi, Nasushiobara (JP); Mariko Shibata, Nasushiobara (JP); Toshie Maruyama, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 199 days.

(21) Appl. No.: 15/383,910

(22) Filed: Dec. 19, 2016

(65) Prior Publication Data

US 2017/0172531 A1    Jun. 22, 2017

(30) Foreign Application Priority Data

Dec. 21, 2015 (JP) .................................. 2015-249074
Dec. 13, 2016 (JP) .................................. 2016-241205

(51) Int. Cl.
*G06T 11/00* (2006.01)
*G06T 7/00* (2017.01)
*A61B 6/00* (2006.01)
*A61B 6/04* (2006.01)
*A61B 6/08* (2006.01)

(52) U.S. Cl.
CPC ............ *A61B 6/502* (2013.01); *A61B 6/0414* (2013.01); *A61B 6/08* (2013.01); *A61B 6/465* (2013.01); *A61B 6/5217* (2013.01)

(58) Field of Classification Search
CPC ........ A61B 6/0414; A61B 6/502; A61B 6/025
See application file for complete search history.

(56) References Cited

U.S. PATENT DOCUMENTS

| 2010/0054402 A1* | 3/2010 | Fischer ..................... A61B 6/08 378/37 |
| 2012/0321161 A1 | 12/2012 | Ishikawa et al. |
| 2013/0064437 A1 | 3/2013 | Meetz et al. |
| 2015/0228093 A1* | 8/2015 | Miyasa ..................... G06T 7/33 382/131 |
| 2016/0110875 A1 | 4/2016 | Sugiyama et al. |

FOREIGN PATENT DOCUMENTS

| JP | 2013-398 | 1/2013 |
| JP | 2013-532001 | 8/2013 |
| JP | 5591309 | 9/2014 |
| JP | 2015-27450 | 2/2015 |

* cited by examiner

*Primary Examiner* — Don K Wong
(74) *Attorney, Agent, or Firm* — Oblon, McClelland, Maier & Neustadt, L.L.P.

(57) ABSTRACT

According to one embodiment, a mammography apparatus includes an X-ray, an imaging stage, a pressing plate, a guide information generator, and an X-ray detection unit. The X-ray tube generates X-rays. The imaging stage supports a breast. The pressing plate presses the breast supported on the imaging stage. The guide information generator provides the imaging stage with guide information for guiding a placement position of the breast. The guide information is generated based on a nipple position, an image start position, and an image end position of a previous image of the breast. The X-ray detection unit generates X-ray projection data by detecting X-rays transmitted through the breast by an X-ray detector.

13 Claims, 15 Drawing Sheets

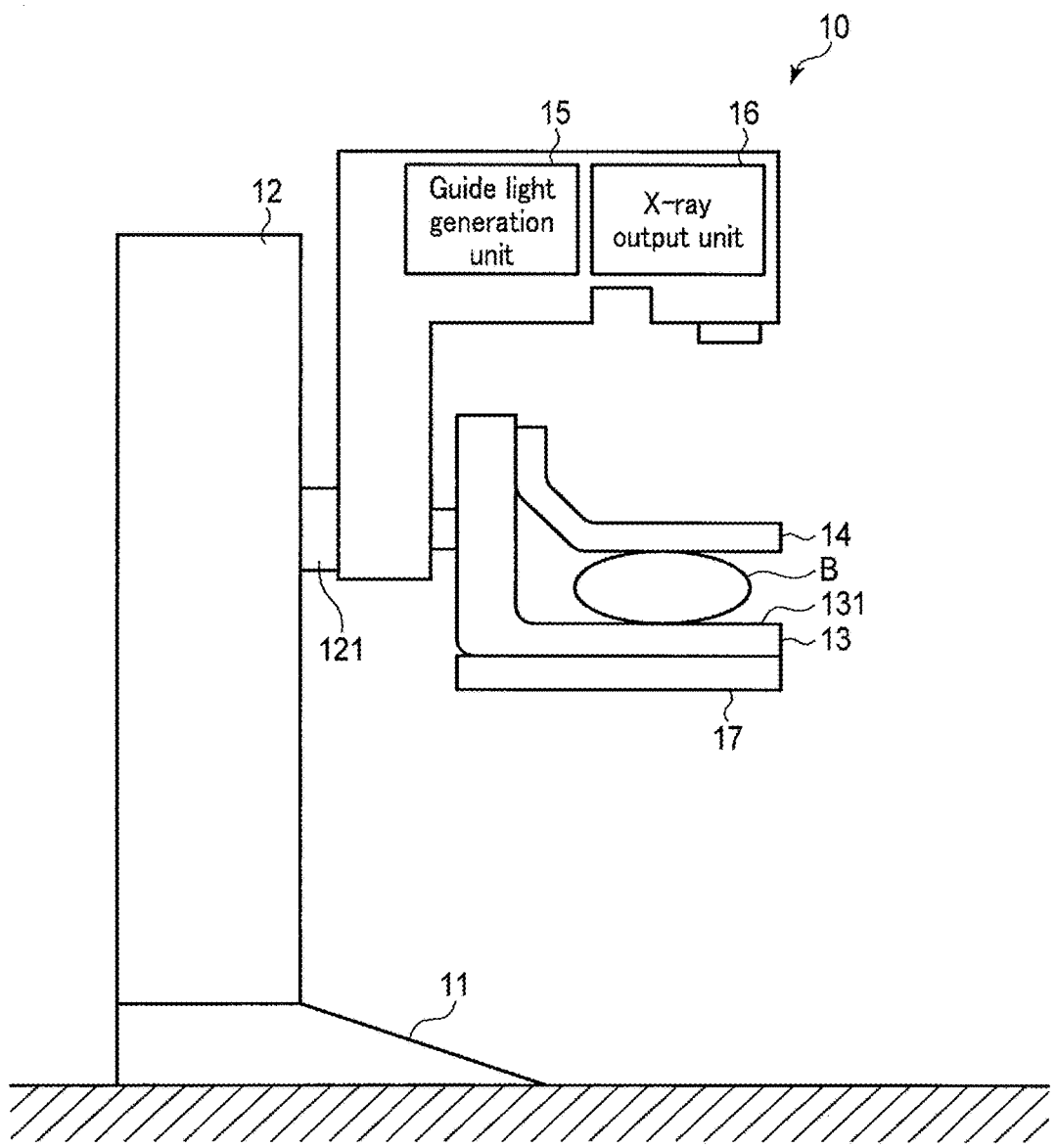
F I G. 2

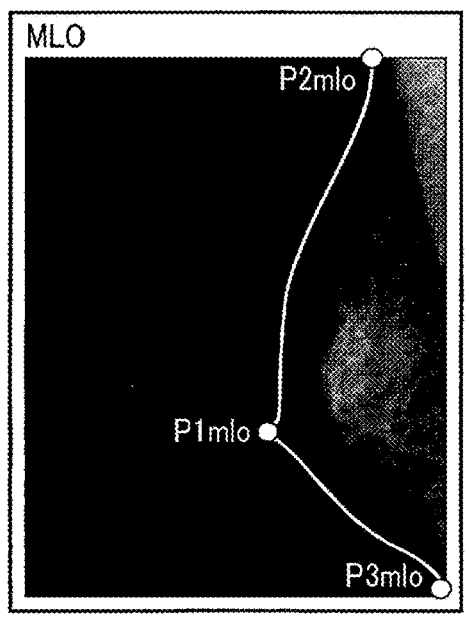
F I G. 9
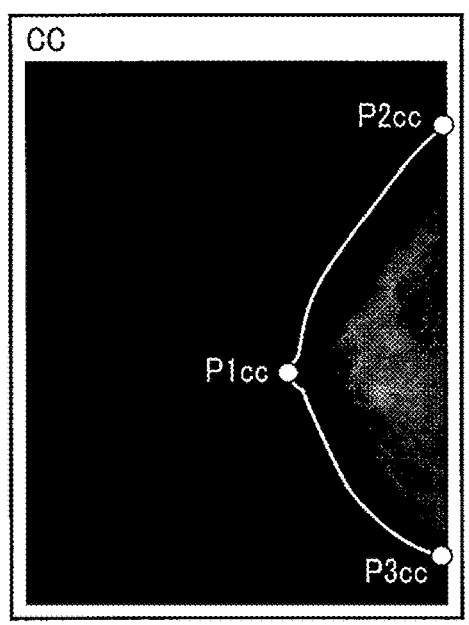
F I G. 10

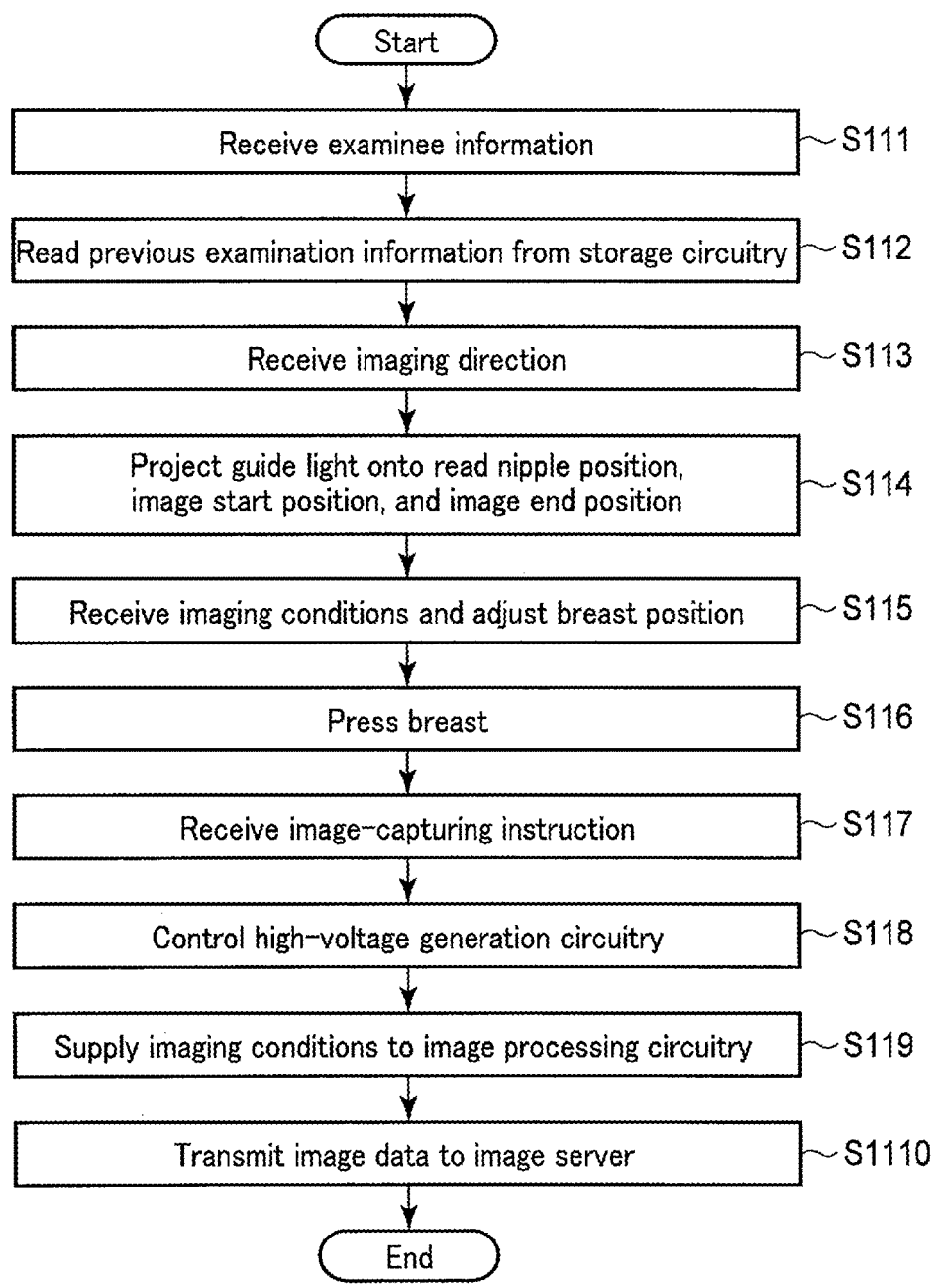
F I G. 11

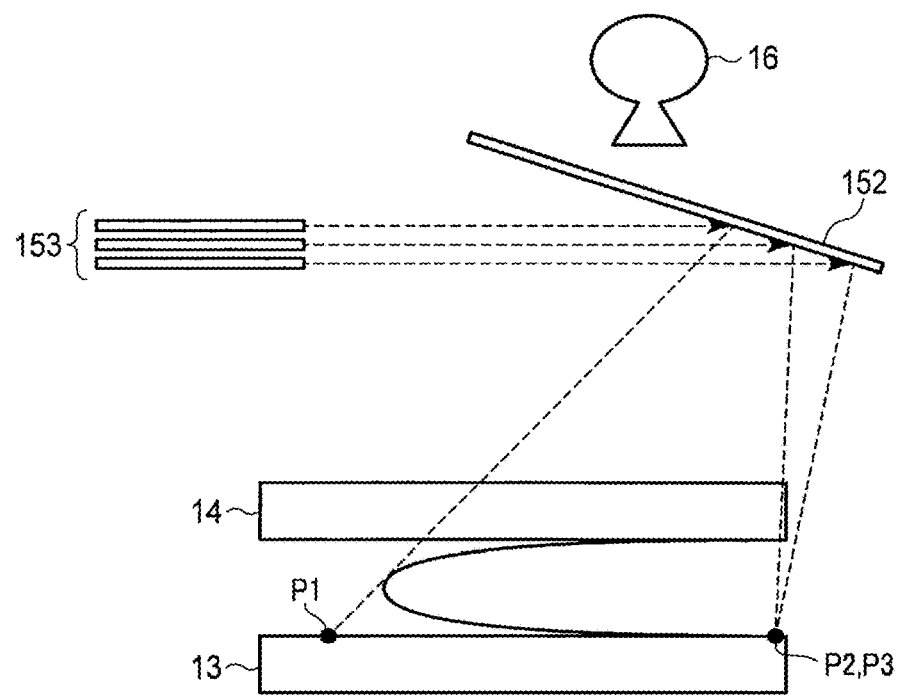
F I G. 12
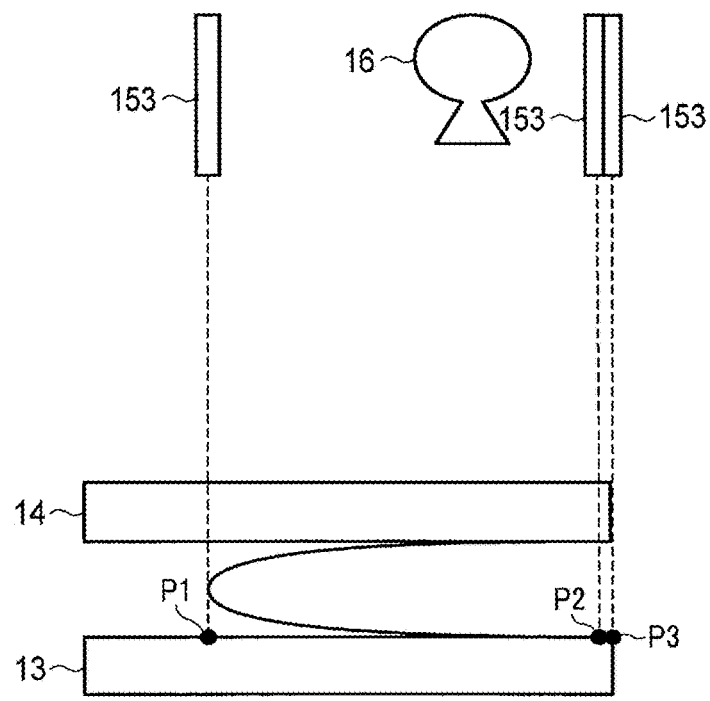
F I G. 13

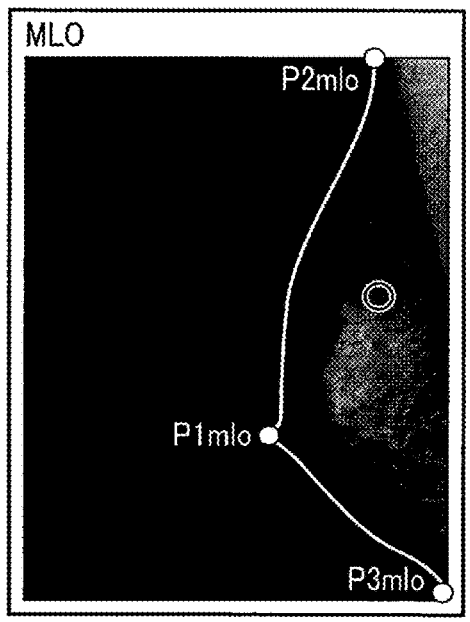
F I G. 14
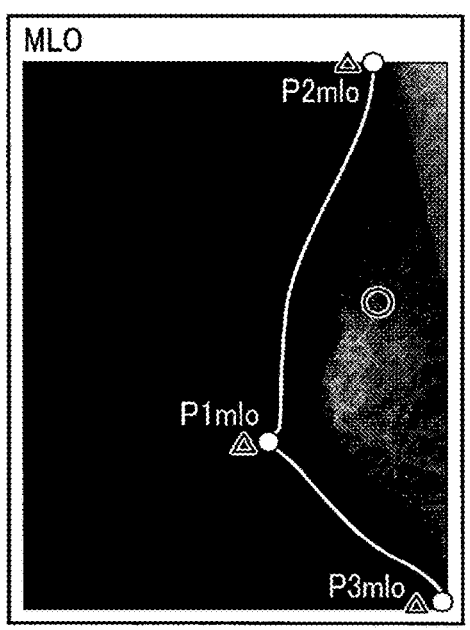
F I G. 15

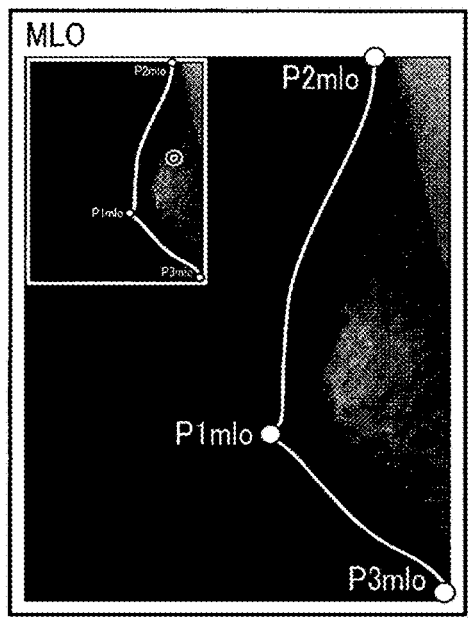
F I G. 16
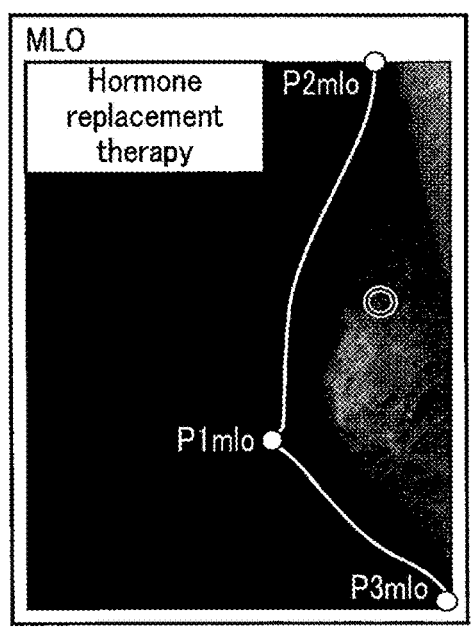
F I G. 17

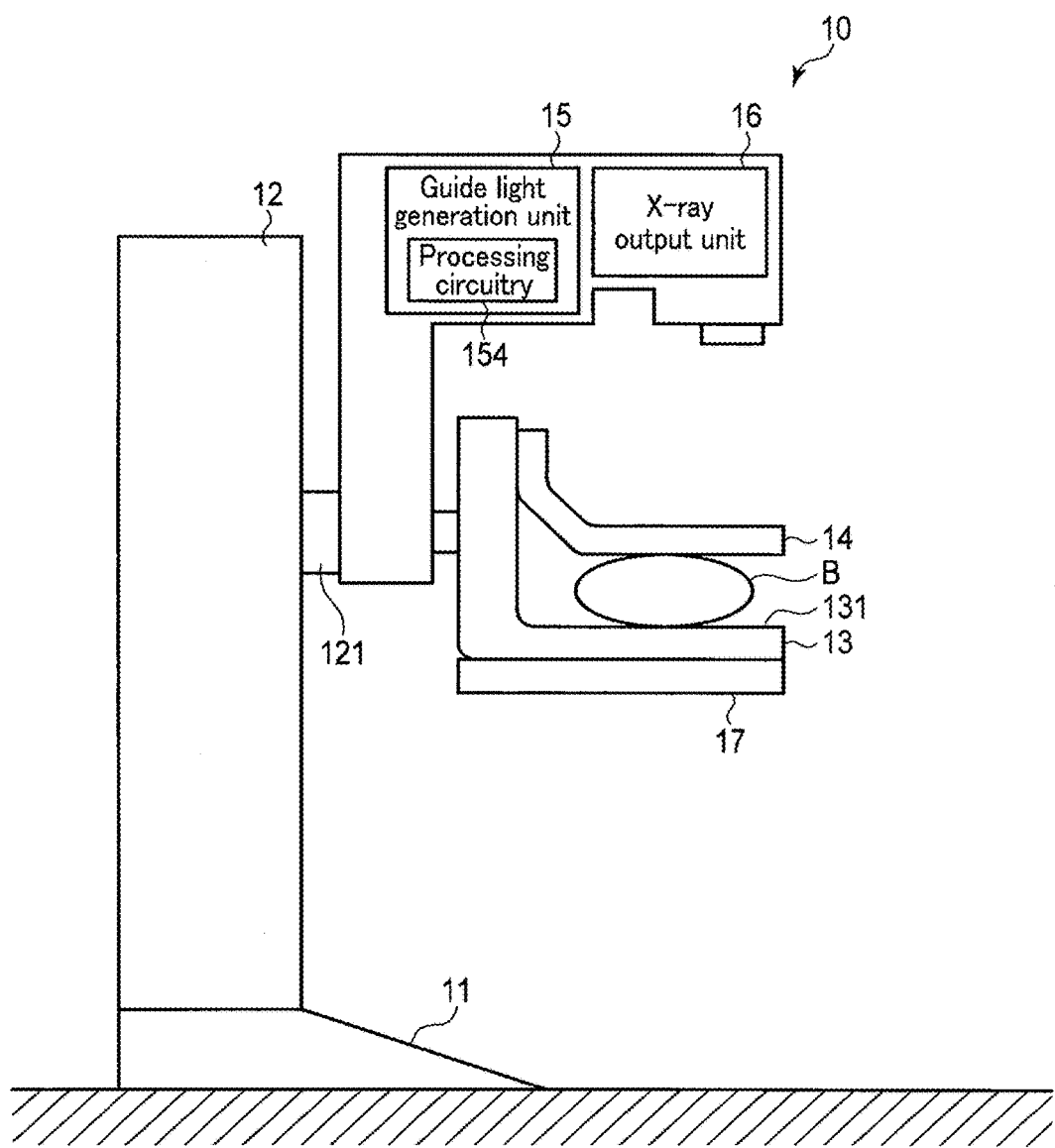
F I G. 18

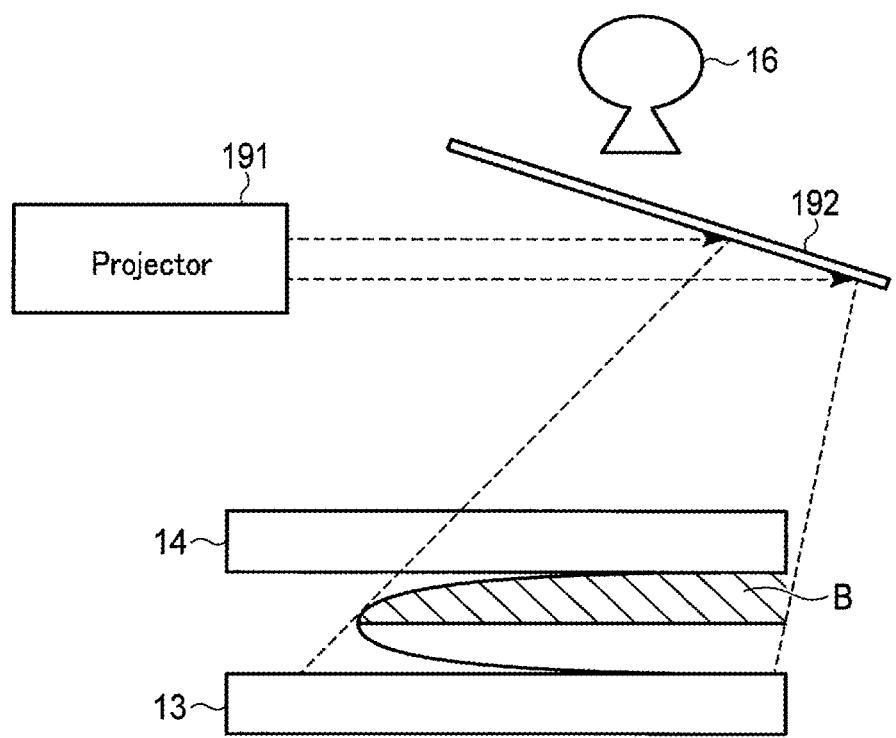
F I G. 21

MAMMOGRAPHY APPARATUS

CROSS-REFERENCE TO RELATED APPLICATIONS

This application is based upon and claims the benefit of priority from prior Japanese Patent Application No. 2015-249074, filed Dec. 21, 2015 and No. 2016-241205, filed Dec. 13, 2016, the entire contents of both which are incorporated herein by reference.

FIELD

Embodiments described herein relate generally to a mammography apparatus.

BACKGROUND

A mammography apparatus is a standard image diagnostic apparatus used in mammary gland image examination. In the mammary gland image examination, mammography images taken by a mammography apparatus are used.

The mammary gland image examination is performed in breast cancer screening, which asymptomatic women are recommended to undergo, for example, once a year or once in several years. An image interpreter examines the mammography images taken by the mammography apparatus to check for microcalcifications, tissue disorders, tumor masses, focal asymmetric densities (FAD), or the like.

The mammary gland image examination is also performed in the follow-up examination for women who have a symptom of breast cancer. The image interpreter examines the mammography images to check for an affected portion or a region of interest (ROI).

In the mammary gland image examination, positioning is important. The positioning has an effect on how to press a breast by a pressing plate of the mammography apparatus, namely, how to spread mammary glands. Thus the mammography images vary depending on the positioning. The variation of the mammography images causes the difference of the positions of the affected portion and ROI between newly-taken mammography image and previously-taken mammography image.

If the positions of the affected portion and ROI are different, the image interpreter has to consider the positioning difference when examining how the mammography images changed with time from previously-taken images. As a result, the efficiency of image interpretation may be lowered.

BRIEF DESCRIPTION OF THE DRAWINGS

FIG. 2 is a diagram showing a configuration of the mammography apparatus shown in FIG. 1.

FIG. 9 is a drawing showing an MLO image which is displayed on the display circuitry shown in FIG. 5.

FIG. 10 is a drawing showing a CC image which is displayed on the display circuitry shown in FIG. 5.

FIG. 11 is a flowchart showing a procedure by which the system control circuitry shown in FIG. 5 controls the guide light generation unit to emit guide light.

FIG. 12 is a diagram showing another configuration of the guide light generation unit shown in FIG. 2.

FIG. 13 is a diagram showing still another configuration of the guide light generation unit shown in FIG. 2.

FIG. 14 is a drawing showing another example of an MLO image which is displayed on the display circuitry shown in FIG. 5.

FIG. 15 is a drawing showing another example of an MLO image which is displayed on the display circuitry shown in FIG. 5.

FIG. 16 is a drawing showing still another example of an MLO image which is displayed on the display circuitry shown in FIG. 5.

FIG. 17 is a drawing showing a further example of an MLO image which is displayed on the display circuitry shown in FIG. 5.

FIG. 18 is a diagram showing an another configuration of the mammography apparatus shown in FIG. 2.

FIG. 21 is a diagram showing how positioning is performed when the projection image is projected onto the pressing plate and the imaging stage shown in FIG. 19.

DETAILED DESCRIPTION

In general, according to one embodiment, a mammography apparatus includes an X-ray, an imaging stage, a pressing plate, a guide information generator, and an X-ray detection unit. The X-ray tube generates X-rays. The imaging stage supports a breast. The pressing plate presses the breast supported on the imaging stage. The guide information generator provides the imaging stage with guide information for guiding a placement position of the breast. The guide information is generated based on a nipple position, an image start position, and an image end position of a previous image of the breast. The X-ray detection unit generates X-ray projection data by detecting X-rays transmitted through the breast by an X-ray detector.

Hereinafter, embodiments will be described with reference to the accompanying drawings.

Figure 1:
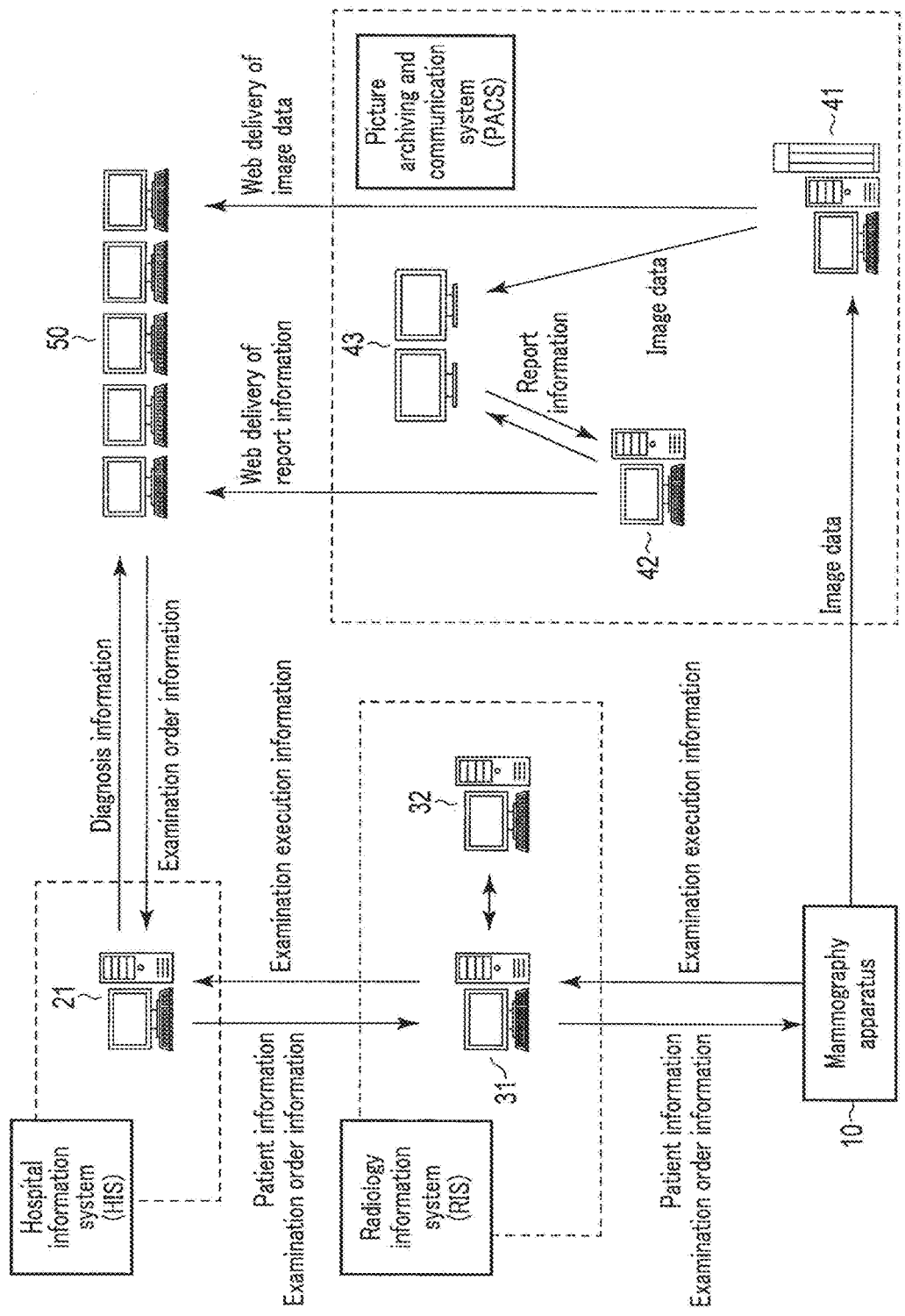
FIG. 1 is a block diagram showing a configuration of a medical information system including a mammography apparatus according to the present embodiment.

FIG. 1 is a block diagram showing a configuration of a medical information system including a mammography apparatus according to the present embodiment. The medical information system depicted in FIG. 1 is provided with a mammography apparatus 10, a hospital information system (HIS) server 21, a radiology information system (RIS) server 31, an RIS terminal 32, an image server 41, a report server 42, a viewer 43 and a PC terminal 50. The mammography apparatus 10, HIS server 21, RIS server 31, RIS terminal 32, image server 41, report server 42, viewer 43 and PC terminal 50 are connected to a local network, and transmit information to a predetermined apparatus and receive information transmitted from the predetermined apparatus by way of the local network. The medical information system may be connected to an external network in addition to the local network or in place thereof.

In FIG. 1, the HIS server 21 is a server constituting a hospital information system (HIS). The RIS server 31 and the RIS terminal 32 are part of the elements constituting a radiation department information management system (RIS). The image server 41, report server 42 and viewer 43 are part of the elements constituting an image management system, namely, a picture archiving and communication system (PACS).

The HIS server 21 electronically manages internal hospital information in the HIS. The internal hospital information includes diagnosis information, patient information, order information, and so on.

It should be noted here that the diagnosis information includes information related to electronic medical charts, such as remark information, disease name information, vital information and examination information. The patient information includes patient IDs, patients' names, sex, age, etc. The order information is information by which a doctor or a medical person asks for a laboratory test, a physiological function test, mammary gland image examination, a prescription for medicine, administration of drugs, or the like. In the description of the present embodiment, the order information will be mentioned as information by which the mammary gland image examination is requested. In this case, the order information includes information on a requester (doctor's name and medical department), a patient ID, and a request to take mammography images.

A specific description will be given of an example of an operation performed by the HIS server 21. The HIS server 21 receives a request for providing diagnosis information of record from the PC terminal 50 used by medical staff including a doctor and a nurse. In response to the request, the HIS server 21 provides the PC terminal with the requested diagnosis information.

From the PC terminal 50, the HIS server 21 also receives order information representing that mammary gland image examination is to be executed. Upon receipt of the order information, the HIS server 21 supplies the order information and the patient information on the patient specified by the order information to the RIS server 31.

The HIS server 21 receives examination execution information transmitted from the RIS server 31. The examination execution information is transmitted from the RIS server 31 when mammary gland image examination is executed using the mammography apparatus 10. The HIS server 21 updates the diagnosis information on the basis of the examination execution information.

The RIS server 31 manages information on radiation examinations in the RIS. The information on radiation examination includes patient's information, order information, image data, etc. The image data includes information on the mammography images previously taken by the mammography apparatus 10. Associated with each mammography image are nipple position information indicative of the position of the nipple of the breast shown in the image, image start position information indicative of the position where the outline of the breast starts in the image, image end position information indicative of the position where the outline of the breast ends in the image, ROI information indicative of the position of a region of interest (ROI), imaging conditions under which the image is taken, etc.

The nipple position, the image start position, and the image end position are calculated by performing image processing after the image is taken. The calculated nipple position, image start position, and image end position are expressed in the coordinates of an X-ray detector 171.

As will be described in detail in connection with the mammography apparatus 10, the imaging conditions are the level of the imaging stage 13 of the mammography apparatus 10 shown in FIG. 2, the angle of rotation of an X-ray output unit 16, the pressing pressure applied by a pressing plate 14, the direction in which the image is taken, etc. A pressing thickness may be used as an imaging condition, replacing the pressing pressure. The pressing thickness indicates the distance between the pressing plate 14 and the imaging stage 13, i.e., the thickness of the pressed and compressed breast. The directions in which an image is taken include the direction of cranio-caudal (CC) projection, the direction of medio-lateral oblique (MLO) projection, etc. If an image is taken by an imaging method that uses a particular imaging direction, the information regarding the imaging method may be used as imaging direction information. In the description below, a mammography image taken by the MLO projection will be referred to as an MLO image, and a mammography image taken by the CC projection will be referred to as a CC image.

Figure 3:
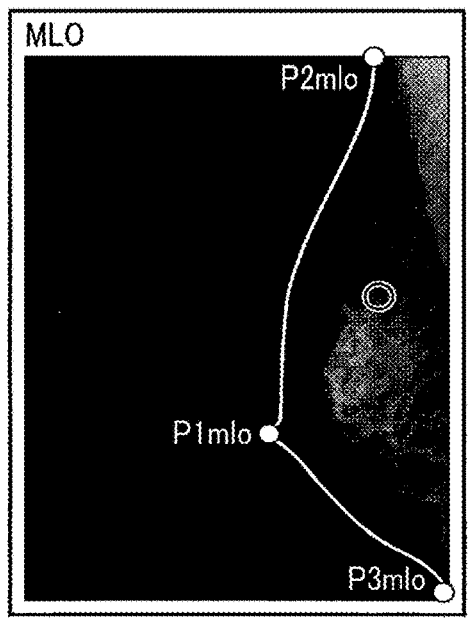
FIG. 3 is a drawing showing an MLO image which is displayed based on image data transmitted from the mammography apparatus shown in FIG. 1.
Figure 4:
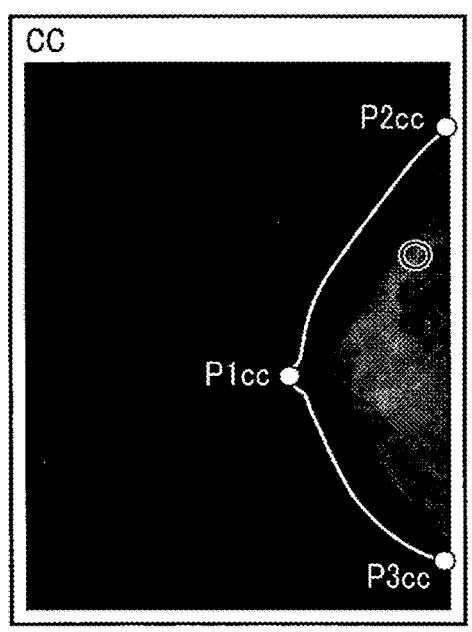
FIG. 4 is a drawing showing a CC image which is displayed based on image data transmitted from the mammography apparatus shown in FIG. 1.

FIGS. 3 and 4 show examples of images that are displayed based on image data according to the present embodiment. FIG. 3 shows an MLO image on which indication points indicative of the nipple position P1$mlo$, image start position P2$mlo$, image end position P3$mlo$ and ROI are superimposed. FIG. 4 shows a CC image on which indication points indicative of the nipple position P1$cc$, image start position P2$cc$, image end position P3$cc$ and ROI are superimposed.

The image data are compliant with the digital image and communication medicine (DICOM) standard and are managed by the PACS. The mammography images are stored in the value field of image data, and the nipple position information, the image start position information, the image end position information, the ROI information, and the imaging conditions are stored in the private tag of the image data. The method in which the nipple position information, the image start position information, the image end position information, the ROI information, and the imaging conditions are associated with the mammography images is not limited to the method described above. For example, the nipple position information, the image start position information, the image end position information, the ROI information, and the imaging conditions, etc. may be managed as individual parameter data. In this case, the parameter data are associated with the image data in which the mammography images are stored.

A specific description will be given of an example of an operation performed by the RIS server 31. Upon receipt of the patient information and order information from the HIS server 21, the RIS server 31 acquires image data associated with the patient specified by the patient information from the image server 41. The RIS server 31 reads the nipple position information, image start position information, image end position information, ROI information, imaging conditions, etc. from the private tag of the acquired image data.

The RIS server 31 receives a radiation examination request based on the order information from the RIS terminal 32. The RIS server 31 refers to the radiation examination request, nipple position information, image start position information, image end position information, ROI information, imaging conditions, etc. and prepares an imaging order regarding the imaging of an examinee. The imaging order includes, for example, information on a requester (doctor's name and medical department), a patient ID, a body portion to be imaged, a radiation intensity, a date of examination, a radiographer's name, a nipple position, an image start position, an image end position, an ROI, and image conditions. The RIS server 31 transmits the patient information and the imaging order to the mammography apparatus 10.

In addition, the RIS server 31 receives examination execution information transmitted from the mammography apparatus 10. The RIS server 31 transmits the received examination execution information to the HIS server 21.

The mammography apparatus 10 executes mammary gland image examination, based on the patient information and imaging order transmitted from the RIS server 31. The mammography apparatus 10 irradiates an examinee's breast with X-rays, detects the X-rays transmitted through the breast, and generates a mammography image. The mammography apparatus 10 supplies the generated mammography image to the image server 41.

The image server 41 stores the mammography image generated by the mammography apparatus 10 and outputs it upon request. The viewer 43 displays the mammography image stored in the image server 41 so that an image interpreter can prepare an interpretation report or the like regarding the displayed mammography image. The report server 42 stores the prepared interpretation report and outputs it upon request.

Figure 5:
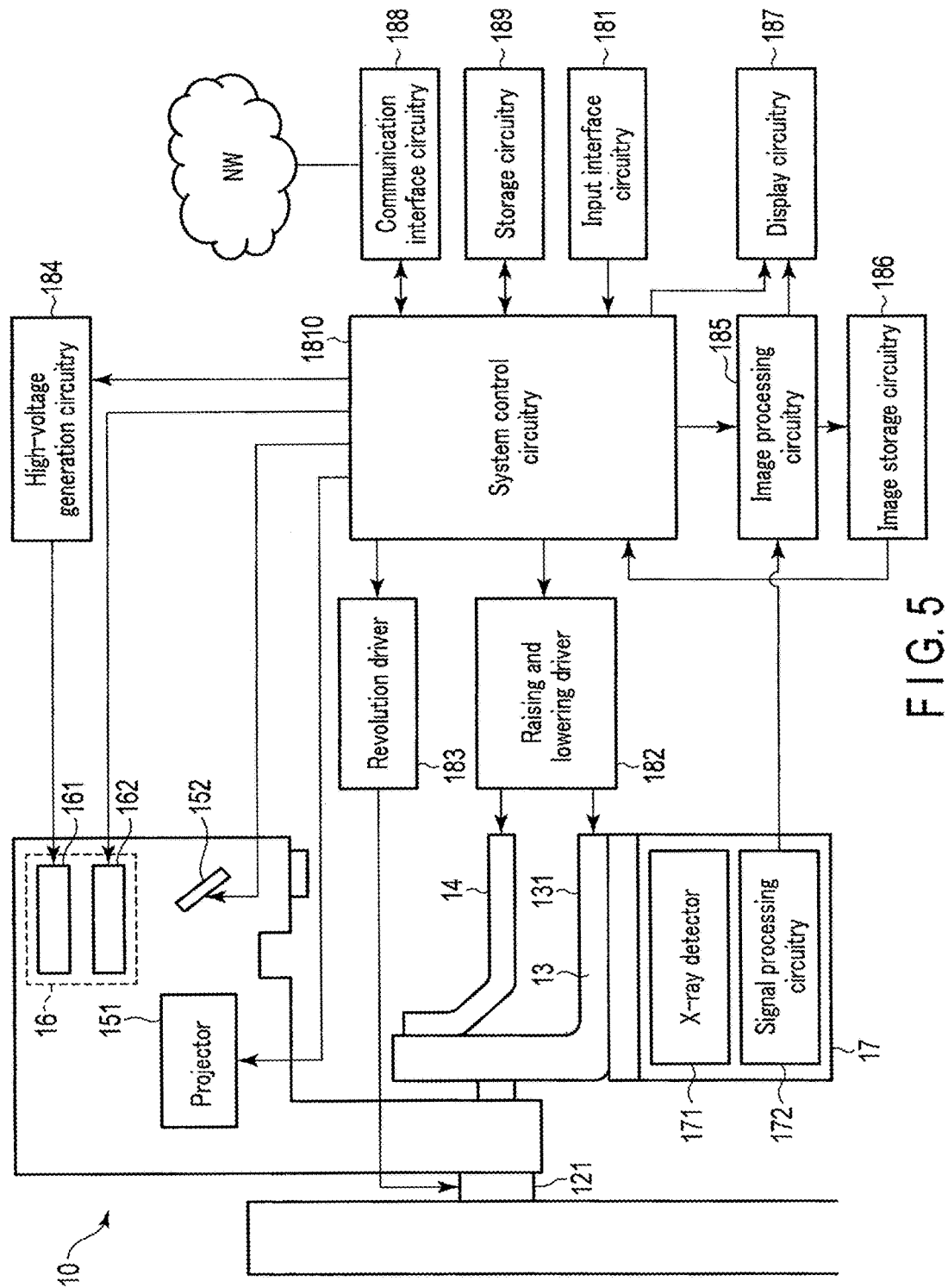
FIG. 5 is a block diagram showing a configuration of the mammography apparatus shown in FIG. 1.

FIG. 2 is a schematic diagram showing a configuration of the mammography apparatus 10 of the present embodiment. FIG. 5 is a block diagram illustrating an exemplary configuration of the mammography apparatus 10 of the embodiment.

As shown in FIG. 2, the mammography apparatus 10 comprises a pedestal 11 and a stand 12. The stand 12 is placed upright on the pedestal 11, and supports the imaging stage 13, pressing plate 14, guide light generation unit 15, X-ray output unit 16, and X-ray detection unit 17. The imaging stage 13, pressing plate 14, and X-ray detection unit 17 are supported such that they are vertically movable. The imaging stage 13, pressing plate 14, guide light generation unit 15, X-ray output unit 16, and X-ray detection unit 17 are supported such that they are rotatable around a support shaft 121.

The imaging stage 13 is a base for supporting an examinee's breast B and has a supporting surface 131 on which the breast B is placed.

The pressing plate 14 is made of a transparent member, for example, an acrylic plate. The pressing plate 14 is arranged above the imaging stage 13 and faces the imaging stage 13 in parallel thereto. The pressing plate 14 is movable closer to or away from the imaging stage 13. When the pressing plate 14 is moved closer to the imaging stage 13, it presses the breast B supported on the supporting surface 131. Pressed by the pressing plate 14, the breast B is expanded and flattened. As a result, the number of mammary gland overlaps decreases.

The guide light generation unit 15 is an example of a guide information generation unit that generates guide information, and is located in the neighborhood of the X-ray output unit 16. The guide light generation unit 15 projects guide light corresponding to the outline of the breast B onto the pressing plate 14. The guide light is an example of the guide information. The guide light passes through the transparent pressing plate 14 and falls on the supporting surface 131 of the imaging stage 13.

Figure 6:
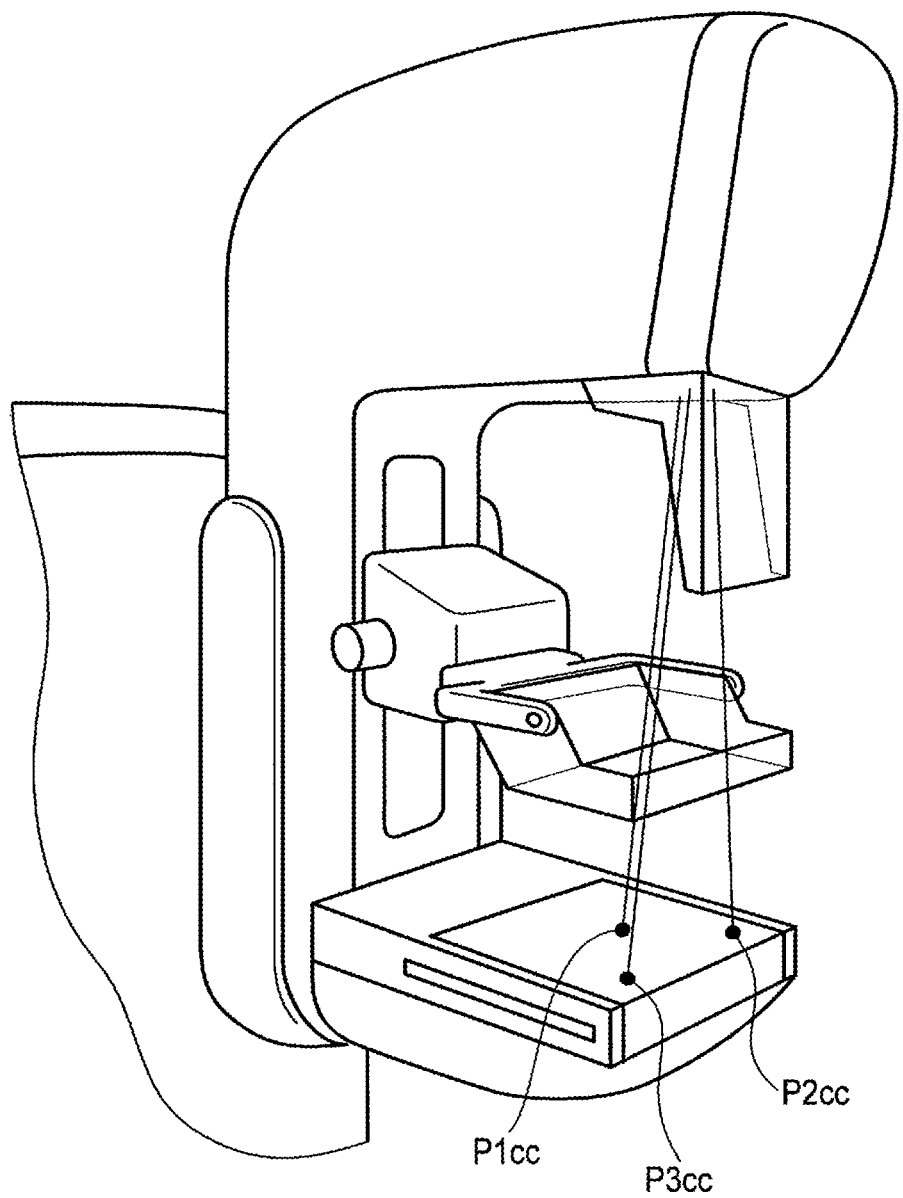
FIG. 6 is a diagram showing guide light projected from the mammography apparatus shown in FIG. 1.
Figure 7:
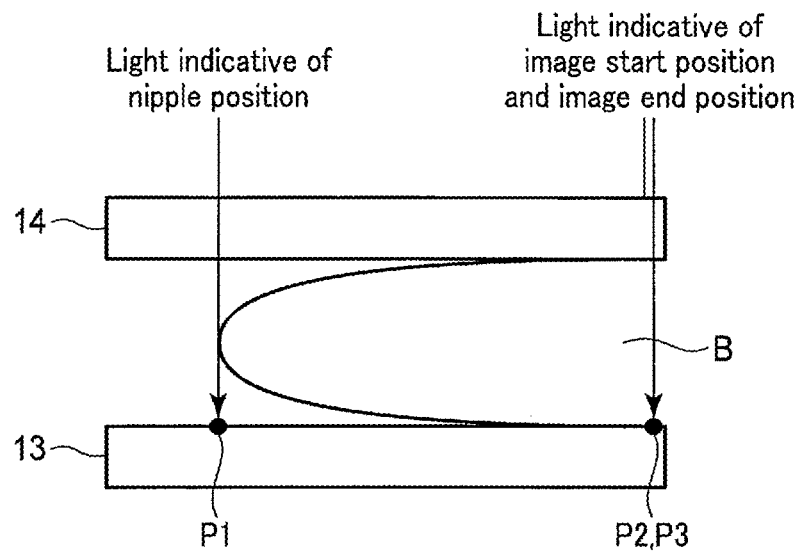
FIG. 7 is a diagram showing how positioning is performed when the guide light is projected onto the pressing plate and the imaging stage shown in FIG. 2.

The guide light is, for example, visible light that indicates the nipple position, image start position, and image end position on the supporting surface 131. As shown, for example, in FIG. 6, the guide light is projected onto the pressing plate 14. Where the guide light is made to pass through the pressing plate 14 and is projected on the imaging stage 13, the guide light should desirably travel in straight lines, without being refracted by the pressing plate 14. As shown in FIG. 7, the radiographer adjusts the positioning in such a manner that the nipple of the breast B is at irradiation position P1 on the supporting surface 131 and the base of the breast B is at positions P2 and P3.

The X-ray output unit 16 irradiates the breast B pressed by the pressing plate 14 with X-rays.

The X-ray detection unit 17 detects the X-rays passing through the breast B and generates X-ray projection data on the basis of the detected X-rays.

As shown in FIG. 5, the mammography apparatus 10 comprises an input interface circuitry 181, a raising and lowering driver 182, a revolution driver 183, a high-voltage generation circuitry 184, an image storage circuitry 186, a display circuitry 187, a communication interface circuitry 188, a storage circuitry 189, and a system control circuitry 1810.

The input interface circuitry 181 includes, for example, a mouse, a keyboard, a button, a panel switch, a touch command screen, a track ball, and a joy stick, etc. The input interface circuitry 181 is connected to the system control circuitry 1810 and supplies the system control circuitry 1810 with various instructions, commands, and information entered by the radiographer. Note that in this specification, the input interface circuitry 181 is not limited to circuitry which includes physical operating components such as a mouse and a keyboard. For example, the input interface circuitry 181 includes, as an example, electrical signal processing circuitry which receives an electrical signal corresponding to an operation instruction input from an external input device provided separately from the mammography apparatus 10 and outputs the electrical signal to the system control circuitry 1810.

The raising and lowering driver 182 is realized, for example, by a gear, a stepping motor, a belt conveyor, and a lead screw, etc., and is connected to the imaging stage 13 and the pressing plate 14. The raising and lowering driver 182 moves the imaging stage 13 in accordance with the position information on the imaging stage 13, which is output from the system control circuitry 1810. The raising and lowering driver 182 moves the pressing plate 14 in accordance with the position information on the pressing plate 14, which is output from the system control circuitry 1810.

The revolution driver 183 is realized, for example, by a gear, a stepping motor, a belt conveyor, and a lead screw, etc., and is connected to the support shaft 121. The revolution driver 183 revolves the support shaft 121 in accordance with the revolution angle information on the support shaft 121, which is output from the system control circuitry 1810.

Figure 8:
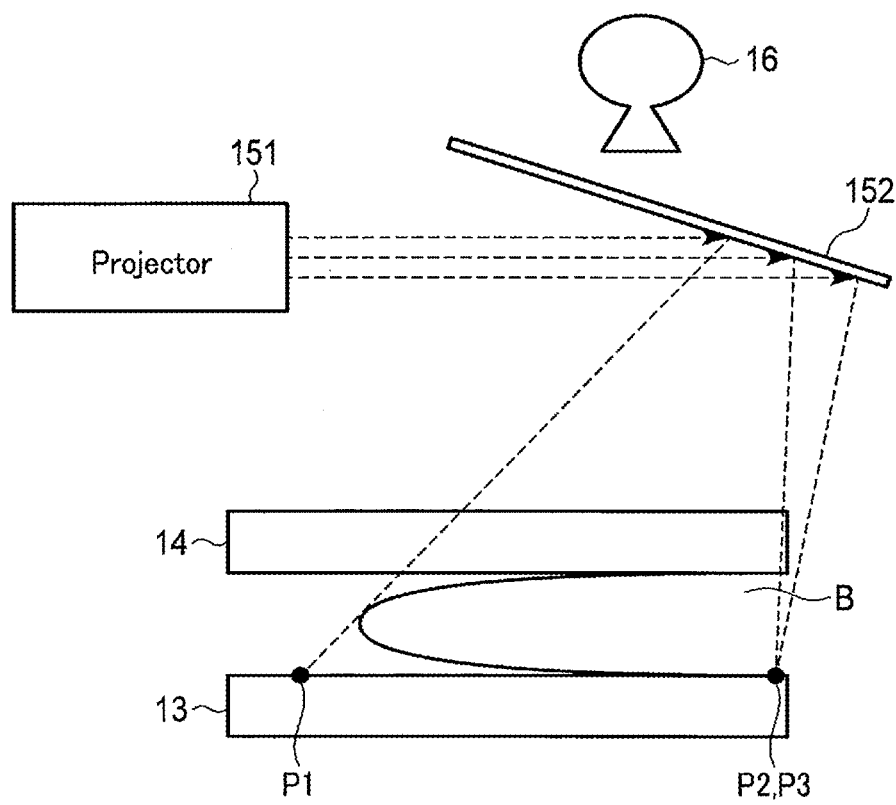
FIG. 8 is a diagram showing a configuration of the guide light generation unit shown in FIG. 1.

The guide light generation unit 15 comprises a projector 151 and a reflector 152. FIG. 8 is a schematic diagram showing an exemplary configuration of the guide light generation unit 15 of the present embodiment. The projector 151 is an example of a light source and emits visible light to the reflector 152 in accordance with an irradiation pattern output from the system control circuitry 1810. The irradiation pattern includes coordinate information and pixel information so that positions on the supporting surface 131 corresponding to the nipple position, image start position, and image end position are irradiated with visible light. The visible light emitted from the projector 151 may indicate the nipple position, image start position, and image end position, using a single color or different colors. The reflector 152 reflects the visible light emitted from the projector 151 in such a manner that the reflected light travels in the direction designated by the system control circuitry 1810.

The X-ray output unit 16 comprises an X-ray tube 161 and an X-ray converging device 162. A high-voltage generation circuitry 184 is connected to the X-ray tube 161. The high-voltage generation circuitry 184 applies the X-ray tube 161 with a voltage having a level designated by the system control circuitry 1810. The X-ray tube 161 generates X-rays, using the high voltage applied by the high-voltage generation circuitry 184. The X-ray converging device 162 is arranged between the X-ray tube 161 and the pressing plate 14. In accordance with an instruction from the system control circuitry 1810, the X-ray converging device 162 controls the irradiation range irradiated with the X-rays generated by the X-ray tube 161.

The X-ray detection unit 17 comprises an X-ray detector 171 and a signal processing circuitry 172. The X-ray detector 171 detects the X-rays passing through the breast B and the imaging stage 13 and converts the detected X-rays into an electric signal (transmission X-ray data). The signal processing circuitry 172 generates X-ray projection data from the electric signal obtained by the X-ray detector 171.

The image processing circuitry 185 is a processor which realizes predetermined functions by reading an operating program from the storage circuitry 189 and executing the read program. The image processing circuitry 185 generates a mammography image based on the X-ray projection data generated by the signal processing circuitry 172. As a result, an MLO image or a CC image is generated.

The image processing circuitry 185 analyzes the generated MLO image and acquires nipple position P1$mlo$, image start position P2$mlo$, and image end position P3$mlo$ on the MLO image.

To be more specific, the image processing circuitry 185 extracts the nipple position P1$mlo$ from the MLO image. The image processing circuitry 185 determines an X_MLO axis, a Y_MLO axis, and an origin of the X-ray detector 171 on the MLO image. For example, of the four corner points of the rectangular detection surface of the X-ray detector 171, the corner point that is included in the two corner points closer to the examinee and that is located on the upper side of the breast is set as an origin by the image processing circuitry 185. In addition, the image processing circuitry 185 detects the skin surface S_MLO on the MLO image. Various known image detection methods may be used as a method for detecting the skin surface S_MLO.

Between the two points where the detected skin surface S_MLO contacts the X_MLO axis, Y_MLO axis, or the predetermined maximal value on the Y_MLO axis, the point closer to the origin is set as an image start position P2$mlo$, and the point farther from the origin is set as an image end position P3$mlo$. The image processing circuitry 185 may receive radiographer's instructions designating the image start position P2$mlo$ and image end position P3$mlo$, and set the positions based on the received instructions.

The image processing circuitry 185 analyzes the generated CC image and acquires nipple position P1$cc$, image start position P2$cc$, and image end position P3$cc$ on the CC image.

To be more specific, the image processing circuitry 185 extracts a nipple position P1$cc$ from the CC image. The image processing circuitry 185 determines an X_CC axis, a Y_CC axis, and an origin of the X-ray detector 171 on the CC image. For example, of the four corner points of the rectangular detection surface of the X-ray detector 171, the corner point that is included in the two corner points closer to the examinee and that is located on the outer side of the breast is set as an origin by the image processing circuitry 185. In addition, the image processing circuitry 185 detects the skin surface S_CC on the CC image. Like the detection of skin surface S_MLO, various known image detection methods may be used as a method for detecting skin surface S_CC.

Between the two points where the detected skin surface S_CC contacts the X_CC axis, the point closer to the origin is set as an image start position P2$cc$, and the point farther from the origin is set as an image end position P3$cc$. The image processing circuitry 185 may receive radiographer's instructions designating the image start position P2$cc$ and image end position P3$cc$, and set the positions based on the received instructions.

The image processing circuitry 185 causes the display circuitry 187 to display the generated MLO image in such a manner that the indication point indicative of the nipple position P1$mlo$, the indication point indicative of the image start position P2$mlo$, and the indication point indicative of the image end position P3$mlo$ are superimposed on the MLO image. The image processing circuitry 185 causes the display circuitry 187 to display the generated CC image in such a manner that the indication point indicative of the nipple position P1$cc$, the indication point indicative of the image start position P2$cc$, and the indication point indicative of the image end position P3$cc$ are superimposed on the CC image. FIG. 9 shows an example of an MLO image displayed on the display circuitry 187. FIG. 10 shows an example of a CC image displayed on the display circuitry 187.

The image processing circuitry 185 sets an ROI on a mammography image. To be more specific, the image processing circuitry 185 receives, at the input interface circuitry 181, an instruction which the radiographer enters for designating a range of a discretionary size on a discretionary position on the MLO image or CC image displayed on the display circuitry 187. The image processing circuitry 185 sets the range designated by the radiographer as an ROI.

For example, the image processing circuitry 185 may use the computer aided diagnosis (CAD) function, automatically detect a candidate region of an affected portion and/or a high-density mammary gland region, and set the detected region as an ROI.

The image processing circuitry 185 converts the generated MLO image into image data that are compliant with the DICOM standard. To be specific, the image processing circuitry 185 stores the MLO image in the value field of the image data. In addition, the image processing circuitry 185 receives imaging conditions of the generated MLO image from the system control circuitry 1810 and writes the received imaging conditions in the private tag of the image data, along with information that identifies the patient (such as patient ID), nipple position information indicative of the nipple position P1$mlo$, image start position information indicative of the image start position P2$mlo$, image end position information indicative of the image end position P3$mlo$, and ROI information indicative of the position of the ROI. The image processing circuitry 185 stores the image data in the image storage circuitry 186.

The image processing circuitry 185 converts the generated CC image into image data that are compliant with the DICOM standard. To be specific, the image processing circuitry 185 stores the CC image in the value field of the image data. In addition, the image processing circuitry 185 receives imaging conditions of the generated CC image from the system control circuitry 1810 and writes the received imaging conditions in the private tag of the image data, along with information that identifies the patient (such as patient ID), nipple position information indicative of the nipple position P1cc, image start position information indicative of the image start position P2cc, image end position information indicative of the image end position P3cc, and ROI information indicative of the position of the ROI. The image processing circuitry 185 stores the image data in the image storage circuitry 186.

By way of the network, the communication interface circuitry 188 transmits signals to other apparatuses and receives signals from other apparatuses. For example, the communication interface circuitry 188 receives, by way of the network, patient information and an imaging order transmitted from the RIS server 31. The communication interface circuitry 188 transmits, by way of the network, the image data stored in the image storage circuitry 186 to the image server 41 in accordance with an instruction supplied from the system control circuitry 1810. The communication interface circuitry 188 transmits, by way of the network, the examination execution information to the RIS server 31 in accordance with an instruction supplied from the system control circuitry 1810.

The storage circuitry 189 includes a memory for storing electronic information, a memory controller for controlling the memory, and a peripheral circuitry such as an interface. The memory is, for example, a processor-readable storage medium, such as a magnetic storage medium, an optical storage medium or a semiconductor memory. The storage circuitry 189 stores an operation program executable by the mammography apparatus 10. The storage circuitry 189 reads an operation program in response to a request made by the processor of the mammography apparatus 10.

The storage circuitry 189 stores patient information received by the communication interface circuitry 188 and information included in the imaging order. In accordance with the request made by the system control circuitry 1810, the storage circuitry 189 reads information therefrom.

The storage circuitry 189 stores data on the level of the imaging stage 13, the angle of rotation of the X-ray output unit 156, the pressing pressure of the pressing plate 14, etc. which are determined each time a mammography image is taken. These data are stored as new imaging conditions.

The system control circuitry 1810 is a processor which reads an operating program from the storage circuitry 189 and which executes the read program to control the overall operation of the mammography apparatus 10. A specific operation of the system control circuitry 1810 will be described with reference to FIG. 11. FIG. 11 is a flowchart showing an example of an operation which the system control circuitry performs when a mammography image is taken.

From the input interface circuitry 181, the system control circuitry 1810 receives examinee information for specifying an examinee to be examined (step S111). The examinee information is input to the input interface circuitry 181, for example, by entering a patient ID or selecting an examinee from an examination reservation list. Upon receipt of the examinee information, the system control circuitry 1810 reads the previous (last) examination information on the examinee specified by the examinee information from the storage circuitry 189 (step S112). As a result, nipple position information, image start position information, image end position information, ROI information, and imaging conditions of the last examination are read.

From the input interface circuitry 181, the system control circuitry 1810 receives an imaging direction, such as the MLO direction or the CC direction (step S113).

Based on the read nipple position information, image start position information, image end position information, and ROI information, the system control circuitry 1810 calculates an irradiation pattern of the projector 151 and the orientation direction of the reflector 152 so that visible light having a predetermined size is emitted to the nipple position, image start position, image end position, and ROI in accordance with the imaging direction. The system control circuitry 1810 transmits the irradiation pattern to the projector 151, and designates an orientation direction to the reflector 152. As a result, guide light corresponding to the outer shape of an examinee's breast is emitted from the guide light generation unit 15, and projected onto the pressing plate 14 and the imaging stage 13, based on the examinee's mammography images taken previously (step S114).

The system control circuitry 1810 causes the display circuitry 187 to display the read imaging conditions, and receives input of imaging conditions of the examination to be executed (step S115). The displayed imaging conditions include, for example, the level of the imaging stage 13, the angle of rotation of the X-ray output unit 16, and the pressing pressure of the pressing plate 14. The input imaging conditions include, for example, the level of the imaging stage 13, the angle of rotation of the X-ray output unit 16, and the pressing pressure of the pressing plate 14.

More specifically, the radiographer adjusts the standing position of the examinee and the placement position of the breast, referring to the displayed information and the projected guide light. The radiographer also adjusts the level of the imaging stage 13 and the angle of rotation of the X-ray output unit 16 by operating the input interface circuitry 181, referring to the displayed information and the projected guide light. The radiographer enters the pressure applied by the pressing plate 14, referring to the displayed information. The system control circuitry 1810 obtains position information based on the level of the imaging stage 13 entered from the input interface circuitry 181, and supplies the position information to the raising and lowering driver 182. Likewise, the system control circuitry 1810 obtains rotation angle information based on the angle of rotation of the X-ray output unit 16 entered from the input interface circuitry 181, and supplies the rotation angle information to the revolution driver 183.

After the position of the breast is adjusted, the system control circuitry 1810 presses the placed breast based on the entered pressing pressure (step S116). For example, the system control circuitry 1810 lowers the pressing plate 14 until the pressing pressure applied to the breast becomes equal to the entered pressing pressure. The system control circuitry 1810 supplies the position information on the pressing plate 14 to the raising and lowering driver 182.

When the pressing pressure applied to the breast reaches the entered pressing pressure, the system control circuitry 1810 receives a mammography image-taking instruction (step S117). Upon receiving the instruction for taking a mammography image via the input interface circuitry 181, the system control circuitry 1810 designates a voltage level to the high-voltage generation circuitry 184 based on the radiation intensity included in the examination information read in step S111 (step S118). As a result, the breast B is irradiated with X-rays emitted from the X-ray tube 161, and the X-rays passing through both the breast B and the imaging stage 13 are detected by the X-ray detection unit 17.

The system control circuitry 1810 supplies the image processing circuitry 185 with the patient information stored in the storage circuitry 189 and the imaging conditions entered in the examination performed this time (step S119).

The image processing circuitry 185 generates a mammography image based on the X-ray projection data generated by the X-ray detection unit 17. The image processing circuitry 185 analyzes the generated mammography image to acquire a nipple position, image start position, and image end position in the mammography image. The image processing circuitry 185 accepts the designation of an ROI from the radiographer. The image processing circuitry 185 stores the generated mammography image in the value field of image data and writes the patient information received from the system control circuitry 1810, the imaging conditions, the nipple position information, the image start position information, the image end position information, and the ROI information in the private tag of the image data, thereby acquiring image data. The image processing circuitry 185 stores the acquired image data in the image storage circuitry 186.

The system control circuitry 1810 controls the communication interface circuitry 188 such that the image data stored in the image storage circuitry 186 is transmitted to the image server 41 (step S1110), and ends the processing.

After the end of the mammary gland image examination, the system control circuitry 1810 controls the communication interface circuitry 188 to transmit examination execution information.

As described above, the mammography apparatus 10 of the present embodiment emits the guide light corresponding to the outer shape of an examinee's breast by the guide light generation unit 15 based on the examinee's mammography images taken previously. The mammography apparatus 10 projects the emitted guide light onto the pressing plate 14 and the imaging stage 13 from the guide light generation unit 15. As a result, the mammography apparatus 10 can reproduce the positioning used when the mammography images were taken previously.

Therefore, the mammography apparatus 10 of the present embodiment can assist positioning. Accordingly, the mammography apparatus 10 of the present embodiment improves the reproduction of the ROI position and thus enables the accuracy with which the temporal change is confirmed. In addition, the doctor does not have to consider the positioning difference and can therefore confidently diagnose the patient based on mammography images.

According to the present embodiment, the image processing circuitry 185 stores mammography images in the value field of image data, and stores the nipple position information, image start position information, image end position information, ROI information, and imaging conditions in the private tag of the image data. The image processing circuitry 185 stores the image data in the image storage circuitry 186. The system control circuitry 1810 transmits the image data stored in the image storage circuitry 186 to the image server 41. When a mammography image is taken next time, the mammography apparatus 10 can use the nipple position information, image start position information, image end position information, and imaging information included in the stored image data and can therefore assist positioning.

The above embodiment was described, referring to the case where the guide light generation unit 15 projects guide light indicative of the positions represented by nipple position information, image start position information, and image end position information included in image data. However, the information representing the position of a breast is not limited to the nipple position information, image start position information, and image end position information described above. Information other than the nipple position information, image start position information, and image end position information may be included in the image data, provided that the shape of the breast can be specified by such information. The guide light generation unit 15 can project guide light indicative of the positions represented by such information.

The present embodiment was described, referring to the case where the guide light generation unit 15 comprises a projector 151 and a reflector 152, as shown in FIG. 8. However, this configuration is in no way restrictive. For example, the guide light generation unit 15 may comprise laser pointers 153 and a reflector 152, as shown in FIG. 12. In this case, the system control circuitry 1810 controls the positions of the laser pointers 153 such that the guide light reflected by the reflector 152 is projected, for example, onto the read nipple position, image start position, and image end position. Desirably, the orientation direction of the reflector 152 should be fixed in order to simplify the structure of the guide light generation unit 15.

The guide light generation unit 15 may comprise laser pointers 153 in such a manner as is shown in FIG. 13. In this case, the system control circuitry 1810 controls the positions of the laser pointers 153 such that guide light is projected, for example, onto the read nipple position, image start position, and image end position, with no need to employ a mirror. That is, the light emitted from the laser pointers 153 travels directly to the imaging stage 13 and the pressing plate 14.

The present embodiment was described, referring to the case where the guide light generation unit 15 is provided for the X-ray output unit 16, and projects the guide light onto the imaging stage 13 and the pressing plate from the side of the X-ray output unit 16. However, this configuration is in no way restrictive. That is, the guide light generation unit 15 may be provided for the X-ray detection unit 17. In this case, the guide light generation unit 15 includes, for example, a plurality of LEDs embedded in the imaging stage 13. The LEDs emit light based on instructions supplied from a light emission controller in such a manner that the shape of a breast can be specified.

The present embodiment was described, referring to the case where the mammography apparatus 10 receives an imaging order, including a nipple position, an image start position, an image end position, an ROI, and imaging conditions, etc., from the RIS server 31. However, this configuration is in no way restrictive. From the RIS server 31, the mammography apparatus 10 may receive image data which stores nipple position information, image start position information, image end position information, ROI information, and imaging conditions, etc. in the private tag thereof. In this case, the imaging order does not include a nipple position, an image start position, an image end position, an ROI, or imaging conditions. The system control circuitry 1810 of the mammography apparatus 10 reads the nipple position information, image start position information, image end position information, ROI information, and imaging conditions, etc. from the received image data. The system control circuitry 1810 causes the storage circuitry 189 to store the read nipple position information, image start position information, image end position information, ROI information, and imaging conditions, etc. The system control circuitry 1810 projects guide light based on the information stored in the storage circuitry 189.

From the RIS server 31, the mammography apparatus 10 may read an imaging order including, for example, information on a requester (doctor's name and medical department), a patient ID, a body portion to be imaged, a radiation intensity, an imaging date, and a radiographer, as well as image data including the imaging conditions of the previous imaging. As can be seen from this, the mammography apparatus 10 of the present embodiment can be employed even if the imaging order and image data do not include nipple position information, image start position information, image end position information, or RIO information. The image processing circuitry 185 analyzes the received mammography image, and acquires a nipple position, an image start position, and an image end position in the mammography image. The system control circuitry 1810 causes the storage circuitry 189 to store nipple position information on the acquired nipple position, image start position information on the acquired image start position, image end position information on the acquired image end position, ROI information on the acquired ROI position, and imaging conditions. The system control circuitry 1810 projects guide light based on the information stored in the storage circuitry 189.

The present embodiment was described, referring to the case where the display circuitry 187 displays a mammography image on which the indication points indicative of a nipple position, an image start position, and an image end position are superimposed. However, the indication points superimposed on a mammography image are not limited to these.

For example, the image processing circuitry 185 may superimpose an indication point indicative of an ROI included in an imaging order on a generated mammography image, namely, an indication point indicative of an ROI designated at the time of previous imaging. An example of an MLO image including such an indication point is shown in FIG. 14. The radiographer can refer to the ROI of previous imaging and designate an ROI on a currently-taken mammography image.

The system control circuitry 1810 may project light onto the ROI position designated in the previous imaging. Based on the nipple position information, image start position information, image end position information, and ROI information, the system control circuitry 1810 calculates an irradiation pattern of the projector 151 and the orientation direction of the reflector 152 so that visible light having a predetermined size is emitted to the nipple position, image start position, image end position, and ROI.

The image processing circuitry 185 may superimpose, on the generated mammography image, not only indication points indicative of the nipple position, image start position, and image end position which are acquired based on the generated mammography image, but also indication points indicative of the nipple position, image start position, image end position, and ROI included in the imaging order, namely, the nipple position, image start position, image end position, and ROI of a previously-taken mammography image. An example of an MLO image including such indication points is shown in FIG. 15. The radiographer can be conscious of the previous positioning and designate an ROI on a currently-taken mammography image.

The image processing circuitry 185 may obtain an image by superimposing indication points, indicative of the nipple position, image start position, image end position, and ROI acquired based on a previously-taken mammography image, on the previously-taken mammography image, and superimpose such an image on a currently-taken mammography image. An example of an MLO image including such an image is shown in FIG. 16. As a result, the radiographer can confirm the nipple position, image start position, image end position, and ROI of the previously-taken mammography image and designate an ROI on the currently-taken mammography image.

The previous examination information read by the system control circuitry 1810 may include an age, a height, a weight, a family history, and a medical history, etc. Upon receipt of the examinee information, the system control circuitry 1810 reads information peculiar to the examinee specified by the examinee information from the storage circuitry 189. The system control circuitry 1810 causes the display circuitry 187 to display the read peculiar information, together with the imaging conditions, and waits for input of an imaging condition. As a result, the radiographer can operate the mammography apparatus 10 while referring to the specific information. Let us assume that an examinee was diagnosed as osteoporotic between the last mammary gland image examination and the current mammary gland image examination. When diagnosis information on the osteoporosis is displayed on the display circuitry 187, the radiographer can recognize the necessity of setting the imaging stage 13 at a position lower than that indicated in the imaging order.

The present embodiment was described, referring to the case where image data, in the private tag of which nipple position information, image start position information, image end position information, ROI information, and imaging conditions are written, are stored in the image storage circuitry 186 and transmitted to the image server 41. However, this configuration is in no way restrictive. The information to be written in the private tag may be information other than the nipple position information, image start position information, image end position information, ROI information, and imaging conditions.

For example, the image processing circuitry 185 may write, in the private tag, the ROI information included in the imaging order, namely, ROI information on a previously-designated ROI. As a result, an image interpreter, e.g., a doctor, can interpret a mammography image by comparing the previously-designated ROI and the currently-designated ROI.

The image processing circuitry 185 may write, in the private tag, the nipple position information, image start position information, and image end position information included in the imaging order, namely, the nipple position information, image start position information, and image end position information of a previously-taken mammography image. The image processing circuitry 185 may calculate how the nipple position information, image start position information, and image end position information of a currently-taken mammography image are shifted from those of a previously-taken mammography image, and write the calculated shift in the private tag. As a result, an image interpreter, e.g., a doctor, can interpret the currently-taken mammography image while confirming the nipple position, image start position, and image end position of the previously-taken mammography image.

The image processing circuitry 185 may further write, in the private tag, a previously-taken mammography image and the nipple position information, image start position information, image end position information, and ROI information acquired based on that mammography image. As a result, an image interpreter, e.g., a doctor, can interpret the currently-taken mammography image while confirming the difference between the mammary gland density of the currently-taken mammography image and that of the previously-taken mammography.

The image processing apparatus 185 may further write, in the private tag, the specific information on an examinee, such as the age, height, weight, family history, and medical history of the examinee. As a result, an image interpreter, e.g., a doctor, can interpret the mammography image while referring to the specific information. For example, if the examinee undergoes hormone replacement therapy or chemotherapy, the mammary gland density of that examinee may vary. FIG. 17 shows an example of an MLO image which is displayed on the viewer 43 when hormone replacement therapy is performed. An image interpreter can interpret an MLO image, such as that shown in FIG. 17, in consideration of how the mammary gland density is changed by the hormone replacement therapy. When a predetermined therapy is performed, the image processing circuitry 185 may write, in the private tag, information to the effect that displaying the mammary gland density in an ROI is not proper.

The above embodiment was described, referring to the case where a control signal indicating an irradiation pattern and an orientation direction is supplied from the system control circuitry 1810 to the guide light generation unit 15. However, this configuration is in no way restrictive. The guide light generation unit 15 may comprise a processing circuitry 154, as shown in FIG. 18. In this case, the system control circuitry 1810 supplies nipple position information, image start position information, and image end position information to the processing circuitry 154. Based on the received nipple position information, image start position information, and image end position information, the processing circuitry 154 may calculate the irradiation pattern of the projector 151 and set the orientation direction of the reflector 152.

(Modifications)

In the embodiment described above, the mammography apparatus 10 emits the guide light corresponding to the outer shape of an examinee's breast by the guide light generation unit 15 based on the examinee's mammography images taken previously. Thus the mammography apparatus 10 projects the emitted guide light onto the pressing plate 14 and the imaging stage 13 from the guide light generation unit 15. However, this configuration is in no way restrictive. A mammography apparatus 10A may project a previously-taken mammography image onto the pressing plate 14 and imaging stage 13 as guide information of the positioning of a breast, instead of projecting the guide light described above.

Figure 19:
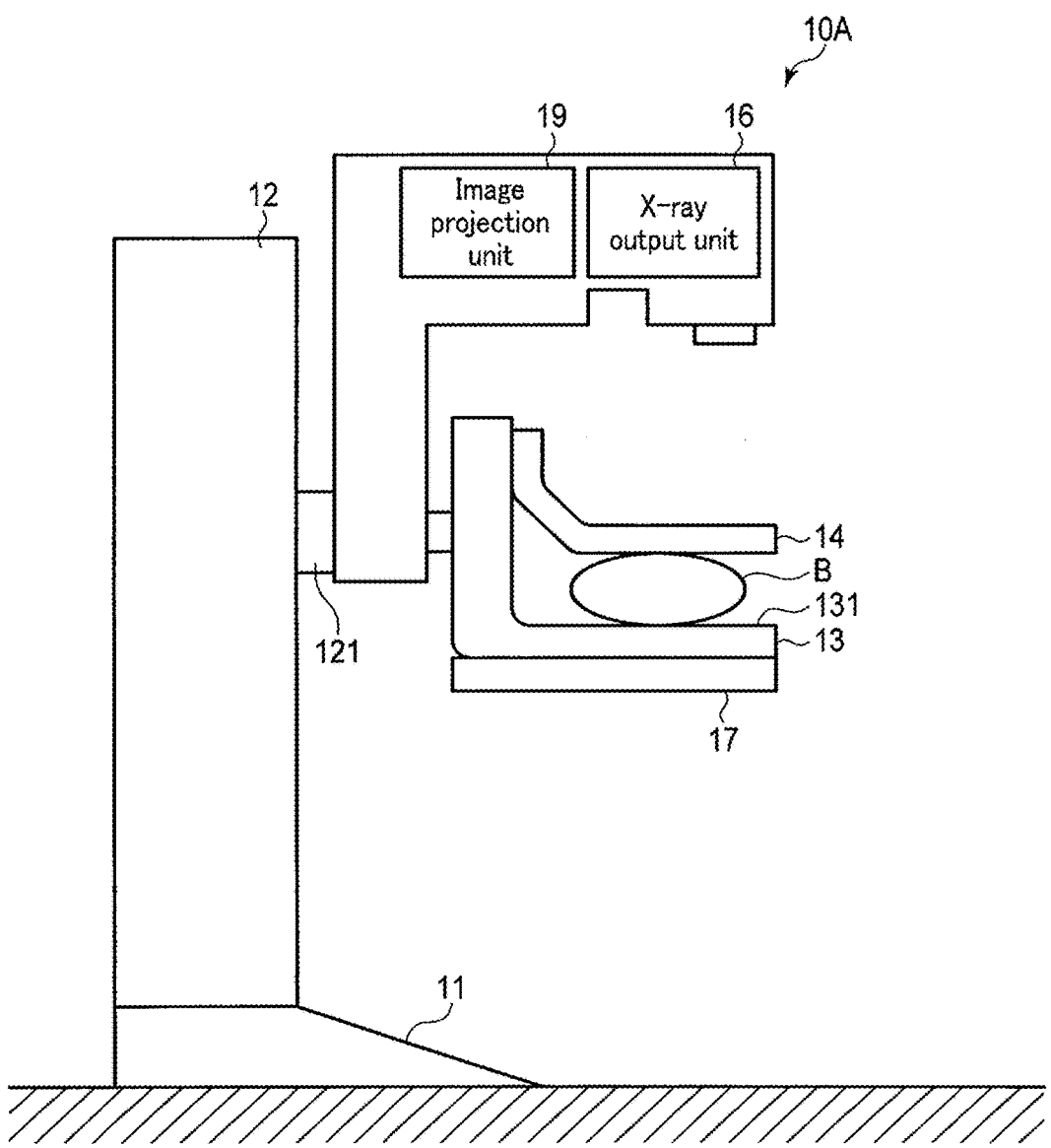
FIG. 19 is a diagram showing a configuration n of a mammography apparatus according to a modification.

As shown in FIG. 19, the mammography apparatus 10A may comprise an image projection unit 19 in place of the guide light generation unit 15 described above and use it as a guide information generator for generating guide information. The image projection unit 19 projects a previously-taken mammography image of a breast B onto the pressing plate 14 and the imaging stage 13. The image projection unit 19 is provided in the neighborhood of the X-ray output unit 16. Like the guide light generation unit 15 shown in FIG. 8, the image projection unit 19 comprises a projector 191 and a reflector 192.

When an examinee undergoing examination is specified, the system control circuitry 1810 of the mammography apparatus 10A acquires a mammography image obtained in the previous (last) examination of the specified examinee, and acquires the nipple position, image start position, and image end position of that mammography image. The nipple position, image start position, and image end position of the mammography image may be acquired by reading them from the storage circuitry 189 or performing image analysis on the mammography image.

The system control circuitry 1810 prepares projection image data for the projector 191 in such a manner that a mammography image can be projected onto the supporting surface 131. The projection image data includes coordinate information and pixel information that enable a mammography image to be projected onto the supporting surface 131. The coordinate information is calculated based on the acquired nipple position, image start position, and image end position.

The system control circuitry 1810 calculates an orientation direction of the reflector 192 based on the acquired nipple position, image start position, and image end position so that the mammography image can be projected onto the supporting surface 131. The system control circuitry 1810 transmits the projection image data to the projector 191 and designates an orientation direction to the reflector 192.

The projector 191 projects the projection image onto the reflector 192 in accordance with the projection image data supplied from the system control circuitry 1810. The reflector 192 reflects the projection image projected from the projector 191 in such a manner that the reflected projection image travels in the direction designated by the system control circuitry 1810. Desirably, the projection image should be projected directly from above the image stage 13 in order that the projection image is not refracted by the pressing plate 14.

Figure 20:
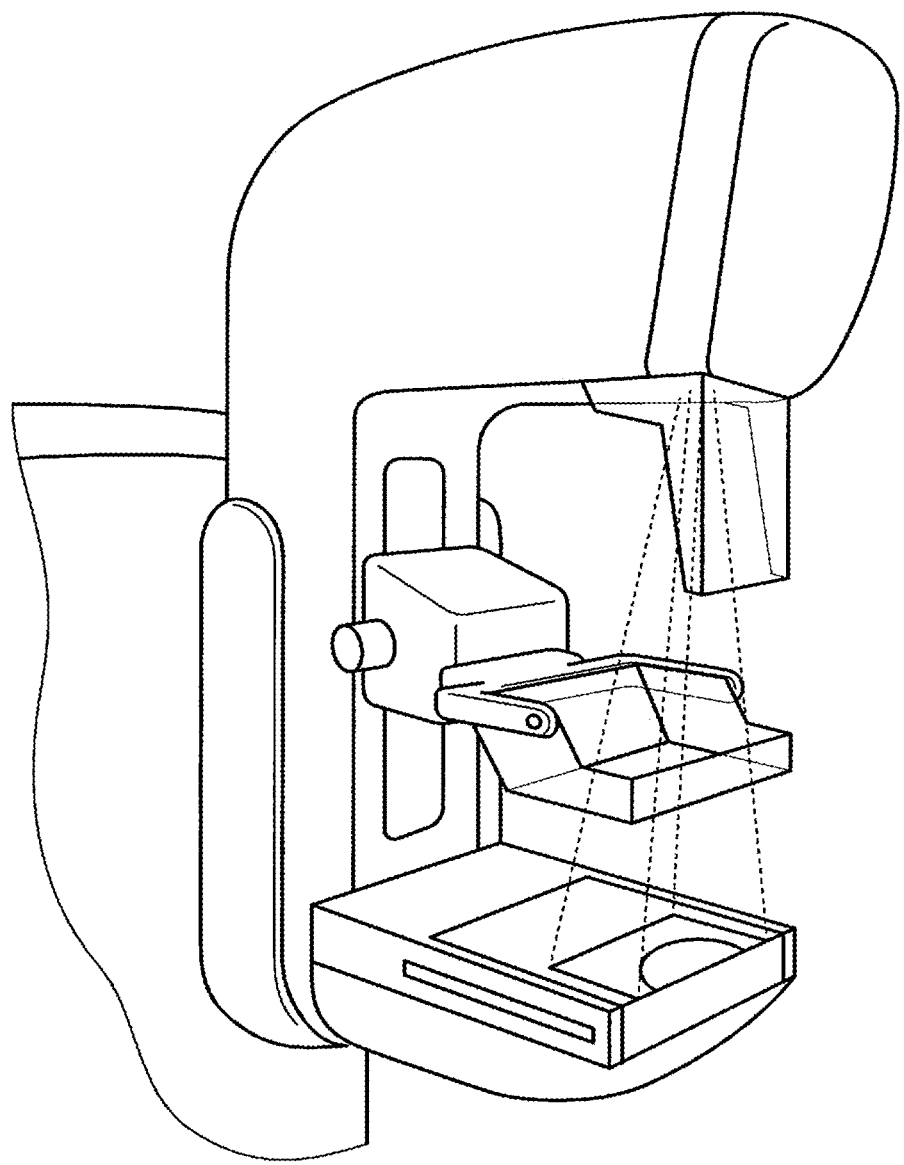
FIG. 20 is a diagram showing a projection image projected from the mammography apparatus shown in FIG. 19.

For example, as shown in FIG. 20, the projection image passes through the transparent pressing plate 14 and is projected onto the supporting surface 131 of the imaging stage 13. As shown in FIG. 21, the radiographer adjusts the positioning in such a manner that the breast B is placed on the projection image projected on the supporting surface 131.

By projecting the previously-taken mammography image of the examinee onto the pressing plate 14 and imaging stage 13, as described above, the mammography apparatus 10 can reproduce the positioning used when the mammography image was taken.

The image processing circuitry 185 of the mammography apparatus 10A generates a mammography image based on the X-ray projection data acquired by irradiating the breast B with X-rays. The image processing circuitry 185 causes the display circuitry 187 to display the generated mammography image.

The image processing circuitry 185 analyzes the generated mammography image to acquire a nipple position, an image start position, and an image end position in the mammography image. The image processing circuitry 185 adjusts the position of the previously-taken mammography image to the position of a newly-taken mammography image. The position adjustment is performed based on the nipple positions, image start positions, and image end positions of the two mammography images. The image processing circuitry 185 increases the transparency of the previously-taken mammography image subjected to the position adjustment, and superimposes the transparency-increased previous mammography image on the mammography image displayed on the display circuitry 187. Because of this superimposed image, the radiographer can be conscious of the previous positioning and designate an ROI on a currently-taken mammography image.

The above modification was described, referring to the case where projection image data and an orientation direction are supplied from the system control circuitry 1810 to the image projection unit 19 as control signals. However, this configuration is in no way restrictive. The image projection unit 19 may be provided with a controller. In this case, the system control circuitry 1810 supplies a mammography image, nipple position information, image start position information, and image end position information to the controller of the image projection unit 19. Based on the received mammography image, nipple position information, image start position information, and image end position information, the controller prepares projection image data of the projector 191 and sets the orientation direction of the reflector 192.

The term "processor" described in the above is intended to refer to a central processing unit (CPU), a graphics processing unit (GPU), an application specific integrated circuit (ASIC), or programmable logic device (e.g., a simple programmable logic device (SPLD), a complex programmable logic device (CPLD), a field programmable gate array (FPGA)), or the like.

Operating programs may be incorporated directly in the processor, instead of storing them in the storage circuitry 189. In this case, the processor reads the operating programs incorporated in its circuitry and executes them to realize the respective functions.

The functions of the image processing circuitry 185 and system control circuitry 1810 shown in FIG. 5 do not have to be realized by processors corresponding to the respective functions. For example, the function of the image processing circuitry 185 and the function of the system control circuitry 1810 may be realized by one processor.

While certain embodiments have been described, these embodiments have been presented by way of example only, and are not intended to limit the scope. Indeed, the novel embodiments described herein may be embodied in a variety of other forms; furthermore, various omissions, substitutions and changes in the form of the embodiments described herein may be made without departing from the spirit. The accompanying claims and their equivalents are intended to cover such forms or modifications as would fall within the scope and spirit.

The invention claimed is:

1. A mammography apparatus, comprising:
    an X-ray tube which generates X-rays;
    an imaging stage which supports a breast;
    a pressing plate which presses the breast supported on the imaging stage;
    a guide information generator configured to provide the imaging stage with guide information represented by points indicative of a nipple position and at least one of an image start position where an outline of the breast starts and an image end position where the outline of the breast ends, wherein the nipple position, the image start position, and the image end position are acquired based on a previous image of the breast; and
    an X-ray detection unit which generates X-ray projection data by detecting X-rays transmitted through the breast by an X-ray detector.

2. The mammography apparatus according to claim 1, wherein the guide information generator is provided for the X-ray tube and comprises:
    a light source which generates guide light; and
    a reflector which reflects the guide light generated by the light source and projects the guide light onto the imaging stage.

3. The mammography apparatus according to claim 1, wherein the guide information generator further provides the imaging stage with guide light that indicates a region of interest designated in the previous image.

4. The mammography apparatus according to claim 1, further comprising:
    image processing circuitry configured to generate a mammography image based on the X-ray projection data generated by the X-ray detection unit, and acquire the nipple position, the image start position, and the image end position from the generated mammography image.

5. The mammography apparatus according to claim 1, further comprising:
    a display which displays imaging conditions under which the previous image is taken.

6. The mammography apparatus according to claim 5, wherein the imaging conditions displayed on the display include a level at which the imaging stage is located when the previous image is taken, an angle of rotation of the X-ray tube when the previous image is taken, and a pressing pressure applied to the breast when the previous image is taken.

7. The mammography apparatus according to claim 5, wherein the imaging conditions displayed on the display include a level at which the imaging stage is located when the previous image is taken, an angle of rotation of the X-ray tube when the previous image is taken, and a thickness to which the breast is pressed when the previous image is taken.

8. The mammography apparatus according to claim 4, further comprising:
    a display which displays the mammography image generated by the image processing circuitry, together with indication points indicative of the nipple position and at least one of the image start position and the image end position.

9. The mammography apparatus according to claim 8, wherein the display further displays an indication point indicative of a region of interest of the previous image.

10. The mammography apparatus according to claim 1, further comprising:
    system control circuitry configured to acquire image data including the previous image, along with a nipple position of the previous image and at least one of the image start position and the image end position of the previous image, and acquire the nipple position and the at least one of the image start position and the image end position from the image data.

11. The mammography apparatus according to claim 5, further comprising:
    system control circuitry configured to acquire image data including the previous image along with the nipple position of the previous image, at least one of the image start position and the image end position of the previous image, and imaging conditions under which the previous image is taken, and acquire the nipple position, at least one of the image start position and the image end position, and the imaging conditions from the image data.

12. The mammography apparatus according to claim 1, further comprising:
    image processing circuitry configured to acquire image data including the previous image and acquire the nipple position and at least one of the image start position and the image end position from the previous image.

13. The mammography apparatus of claim 1, wherein the guide information generator is configured to provide the guide information, which includes only the points indicative of the nipple position, the image start position, and the image end position.

* * * * *